United States Patent [19]
Utsumi et al.

[11] Patent Number: 6,025,329
[45] Date of Patent: Feb. 15, 2000

[54] METHOD FOR TREATING OPHTHALMIC DISEASES

[75] Inventors: Jun Utsumi, Yokohama; Tetsuo Sudo, Kamakura; Yasuhiko Tanaka, Tokyo; Mizuo Matsui, Urawa, all of Japan

[73] Assignee: Toray Industries, Inc., Tokyo, Japan

[21] Appl. No.: 08/817,145

[22] PCT Filed: Jul. 15, 1996

[86] PCT No.: PCT/JP96/01973

§ 371 Date: Jul. 2, 1997

§ 102(e) Date: Jul. 2, 1997

[87] PCT Pub. No.: WO97/05893

PCT Pub. Date: Feb. 20, 1997

[30] Foreign Application Priority Data

Aug. 9, 1995 [JP] Japan .................................. 7-203304

[51] Int. Cl.⁷ .................................................. A61K 38/00
[52] U.S. Cl. .......................................... 514/12; 514/912
[58] Field of Search .............................. 424/78.04, 571, 424/562; 604/295; 514/12, 912; 530/399, 827, 849, 380

[56] References Cited

U.S. PATENT DOCUMENTS 5,455,338 10/1995 Sprecher et al. .

FOREIGN PATENT DOCUMENTS

0563023A1 9/1993 European Pat. Off. .
0564216A2 10/1993 European Pat. Off. .

OTHER PUBLICATIONS

Mizuo, M., Patent Abstracts of Japan, vol. 96, No. 6, Jun. 28, 1996 (JP 08 053362A).

Mizuo, M., Patent Abstracts of Japan, vol. 96, No. 6, Jun. 28, 1996 (JP 08 053495A).

Park et al., Growth Factor–Induced Retinal Regeneration in Vivo, Intl. Rev. Cytology, 146:49–74, 1993.

*Primary Examiner*—Patricia A. Duffy
*Attorney, Agent, or Firm*—Birch, Stewart, Kolasch & Birch, LLP

[57] ABSTRACT

A therapeutic agent for various retinochoroidal diseases such as pigmentary retinal degeneration, retinopathy, maculopathy and retinal detachment is disclosed. The therapeutic agent for ophthalmic diseases according to the present invention comprises as an effective ingredient a retinal pigment epithelial cell growth factor.

6 Claims, 10 Drawing Sheets

| N-terminal Amino Acid Sequence | Asp | Ala | Glu | Gln | Glu | Pro | Thr | Gly | Thr | Asn | Ala | Glu | Ile |
|---|---|---|---|---|---|---|---|---|---|---|---|---|---|
| Primer Sequence 27S1 | GAT<br>C | GCI | GAA<br>G | CAA<br>G | GAA<br>G | CCI<br>G | ACI | G | | | | | |
| 27S2 | | | | CAA<br>G | GAA<br>G | CCI<br>G | ACI | GGI | ACI | AAT<br>C | GC | | |

```
             10         20         30         40        50   54
GGCGCTTTCTCGGACGCCTTGCCCAGCGGCCGCCCGACCCCCTGCACC ATG GAC
                                                 Met Asp 60         70         80         90         96
CCC GCT CGC CCC CTG GGG CTG TCG ATT CTG CTG CTT TTC CTG
Pro Ala Arg Pro Leu Gly Leu Ser Ile Leu Leu Leu Phe Leu 100        110        120        130        138
ACG GAG GCT GCA CTG GGC GAT GCT GCT CAG GAG CCA ACA GGA
Thr Glu Ala Ala Leu Gly Asp Ala Ala Gln Glu Pro Thr Gly 150        160        170        180
AAT AAC GCG GAG ATC TGT CTC CTG CCC CTA GAC TAC GGA CCC
Asn Asn Ala Glu Ile Cys Leu Leu Pro Leu Asp Tyr Gly Pro 190        200        210        222
TGC CGG GCC CTA CTT CTC CGT TAC TAC TAC GAC AGG TAC ACG
Cys Arg Ala Leu Leu Leu Arg Tyr Tyr Tyr Asp Arg Tyr Thr 230        240        250        260  264
CAG AGC TGC CGC CAG TTC CTG TAC GGG GGC TGC GAG GGC AAC
Gln Ser Cys Arg Gln Phe Leu Tyr Gly Gly Cys Glu Gly Asn 270        280        290        300  306
GCC AAC AAT TTC TAC ACC TGG GAG GCT TGC GAC GAT GCT TGC
Ala Asn Asn Phe Tyr Thr Trp Glu Ala Cys Asp Asp Ala Cys 310        320        330        340   348
TGG AGG ATA GAA AAA GTT CCC AAA GTT TGC CGG CTG CAA GTG
Trp Arg Ile Glu Lys Val Pro Lys Val Cys Arg Leu Gln Val 360        370        380        390
AGT GTG GAC GAC CAG TGT GAG GGG TCC ACA GAA AAG TAT TTC
Ser Val Asp Asp Gln Cys Glu Gly Ser Thr Glu Lys Tyr Phe 400        410        420        432
TTT AAT CTA AGT TCC ATG ACA TGT GAA AAA TTC TTT TCC GGT
Phe Asn Leu Ser Ser Met Thr Cys Glu Lys Phe Phe Ser Gly
```

Figure 3B

```
          440             450             460             470   474
GGG TGT CAC CGG AAC CGG ATT GAG AAC AGG TTT CCA GAT GAA
Gly Cys His Arg Asn Arg Ile Glu Asn Arg Phe Pro Asp Glu 480             490             500             510   516
GCT ACT TGT ATG GGC TTC TGC GCA CCA AAG AAA ATT CCA TCA
Ala Thr Cys Met Gly Phe Cys Ala Pro Lys Lys Ile Pro Ser 520             530             540             550       558
TTT TGC TAC AGT CCA AAA GAT GAG GGA CTG TGC TCT GCC AAT
Phe Cys Tyr Ser Pro Lys Asp Glu Gly Leu Cys Ser Ala Asn 570             580             590           600
GTG ACT CGC TAT TAT TTT AAT CCA AGA TAC AGA ACC TGT GAT
Val Thr Arg Tyr Tyr Phe Asn Pro Arg Tyr Arg Thr Cys Asp 610             620             630             642
GCT TTC ACC TAT ACT GGC TGT GGA GGG AAT GAC AAT AAC TTT
Ala Phe Thr Tyr Thr Gly Cys Gly Gly Asn Asp Asn Asn Phe 650             660             670             680   684
GTT AGC AGG GAG GAT TGC AAA CGT GCA TGT GCA AAA GCT TTG
Val Ser Arg Glu Asp Cys Lys Arg Ala Cys Ala Lys Ala Leu 690             700             710             720   726
AAA AAG AAA AAG AAG ATG CCA AAG CTT CGC TTT GCC AGT AGA
Lys Lys Lys Lys Lys Met Pro Lys Leu Arg Phe Ala Ser Arg 730             740             750             760       773
ATC CGG AAA ATT CGG AAG AAG CAA TTT TAA ACATTCTTAATATGTCA
Ile Arg Lys Ile Arg Lys Lys Gln Phe ***

780       790       800       810       820       830
TCTTGTTTGTCTTTATGGCTTATTTGCCTTTATGGTTGTATCTGAAGAATAATATGA 840       850       860       870       880       887
CAGCATGAGGAAACAAATCATTGGTGATTTATTCACCAGTTTTTATTAATACAAGTC
```

Figure 3C

```
       890       900       910       920       930       940 944
ACTTTTTCAAAAATTTGGATTTTTTTATATATAACTAGCTGCTATTCAAATGTGAGT 950       960       970       980       990      1001
CTACCATTTTTAATTTATGGTTCAACTGTTTGTGAGACTGAATTCTTGCAATGCATA 1010      1020      1030      1040      1050      1058
AGATATAAAAGCAAATATGACTCACTCATTTCTTGGGGTCGTATTCCTGATTTCAGA 1070      1080      1090      1100      1110 1115
AGAGGATCATAACTGAAACAACATAAGACAATATAATCATGTGCTTTTAACATATTT 1120      1130      1140
GAGAATAAAAAGGACTAGCAAATAC
```

RPE growth factor cDNA    FLAG sequence

```
         R  K  I  R  K  K  Q  F  D  Y  K  D  D  D  D  K  *  *  KpnI
-5'GGAAAAATTCGGAAGAAGCAATTTGACTACAAGGACGACGATGACAAATGATAAGGTACCCGC3'
-3'CCTTTTAAGCCTTCTTCGTTAAACTGATGTTCCTGCTGCTACTGTTTACTATTCCATGGGCG5'
```

Detailed sequence of junction between RPE growth factor cDNA and FLAG sequence

FIG.5

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 13 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

```
Asp Ala Glu Gln Glu Pro Thr Gly Thr Asn Ala Glu Ile
1               5                   10
```

(2) INFORMATION FOR SEQ ID NO:2:

(i) SEQUENCE CHARACTERISTICS:
      (A) LENGTH: 1140 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 49..753

(xi) SEQUENCE DESCRIPTION: SEQ ID NO:2:

```
GGCGCTTTCT CGGACGCCTT GCCCAGCGGC CGCCCGACCC CCTGCACCAT GGACCCCGCT      60

CGCCCCCTGG GGCTGTCGAT TCTGCTGCTT TTCCTGACGG AGGCTGCACT GGGCGATGCT     120

GCTCAGGAGC CAACAGGAAA TAACGCGGAG ATCTGTCTCC TGCCCCTAGA CTACGGACCC     180

TGCCGGGCCC TACTTCTCCG TTACTACTAC GACAGGTACA CGCAGAGCTG CCGCCAGTTC     240

CTGTACGGGG GCTGCGAGGG CAACGCCAAC AATTTCTACA CCTGGGAGGC TTGCGACGAT     300

GCTTGCTGGA GGATAGAAAA AGTTCCCAAA GTTTGCCGGC TGCAAGTGAG TGTGGACGAC     360

CAGTGTGAGG GGTCCACAGA AAAGTATTTC TTTAATCTAA GTTCCATGAC ATGTGAAAAA     420

TTCTTTTCCG GTGGGTGTCA CCGGAACCGG ATTGAGAACA GGTTTCCAGA TGAAGCTACT     480

TGTATGGGCT TCTGCGCACC AAAGAAAATT CCATCATTTT GCTACAGTCC AAAAGATGAG     540

GGACTGTGCT CTGCCAATGT GACTCGCTAT TATTTTAATC CAAGATACAG AACCTGTGAT     600

GCTTTCACCT ATACTGGCTG TGGAGGGAAT GACAATAACT TTGTTAGCAG GGAGGATTGC     660
```

-continued

```
AAACGTGCAT GTGCAAAAGC TTTGAAAAAG AAAAAGAAGA TGCCAAAGCT TCGCTTTGCC      720

AGTAGAATCC GGAAAATTCG GAAGAAGCAA TTTTAAACAT TCTTAATATG TCATCTTGTT      780

TGTCTTTATG GCTTATTTGC CTTTATGGTT GTATCTGAAG AATAATATGA CAGCATGAGG      840

AAACAAATCA TTGGTGATTT ATTCACCAGT TTTTATTAAT ACAAGTCACT TTTTCAAAAA      900

TTTGGATTTT TTTATATATA ACTAGCTGCT ATTCAAATGT GAGTCTACCA TTTTTAATTT      960

ATGGTTCAAC TGTTTGTGAG ACTGAATTCT TGCAATGCAT AAGATATAAA AGCAAATATG     1020

ACTCACTCAT TTCTTGGGGT CGTATTCCTG ATTTCAGAAG AGGATCATAA CTGAAACAAC     1080

ATAAGACAAT ATAATCATGT GCTTTTAACA TATTTGAGAA TAAAAAGGAC TAGCAAATAC     1140
```

(2) INFORMATION FOR SEQ ID NO:3:

(i) SEQUENCE CHARACTERISTICS:
        (A) LENGTH: 235 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Met Asp Pro Ala Arg Pro Leu Gly Leu Ser Ile Leu Leu Phe Leu
1               5                  10                  15

Thr Glu Ala Ala Leu Gly Asp Ala Ala Gln Glu Pro Thr Gly Asn Asn
            20                  25                  30

Ala Glu Ile Cys Leu Leu Pro Leu Asp Tyr Gly Pro Cys Arg Ala Leu
        35                  40                  45

Leu Leu Arg Tyr Tyr Asp Arg Tyr Thr Gln Ser Cys Arg Gln Phe
50                  55                  60

Leu Tyr Gly Gly Cys Glu Gly Asn Ala Asn Phe Tyr Thr Trp Glu
65                  70                  75                  80

Ala Cys Asp Asp Ala Cys Trp Arg Ile Glu Lys Val Pro Lys Val Cys
                85                  90                  95

Arg Leu Gln Val Ser Val Asp Asp Gln Cys Glu Gly Ser Thr Glu Lys
            100                 105                 110

Tyr Phe Phe Asn Leu Ser Ser Met Thr Cys Glu Lys Phe Phe Ser Gly
        115                 120                 125

Gly Cys His Arg Asn Arg Ile Glu Asn Arg Phe Pro Asp Glu Ala Thr
    130                 135                 140

Cys Met Gly Phe Cys Ala Pro Lys Lys Ile Pro Ser Phe Cys Tyr Ser
145                 150                 155                 160

Pro Lys Asp Glu Gly Leu Cys Ser Ala Asn Val Thr Arg Tyr Tyr Phe
                165                 170                 175

Asn Pro Arg Tyr Arg Thr Cys Asp Ala Phe Thr Tyr Thr Gly Cys Gly
            180                 185                 190

Gly Asn Asp Asn Asn Phe Val Ser Arg Glu Asp Cys Lys Arg Ala Cys
        195                 200                 205

Ala Lys Ala Leu Lys Lys Lys Lys Met Pro Lys Leu Arg Phe Ala
    210                 215                 220

Ser Arg Ile Arg Lys Ile Arg Lys Lys Gln Phe
225                 230                 235
```

(2) INFORMATION FOR SEQ ID NO:4:

(i) SEQUENCE CHARACTERISTICS:
        (A) LENGTH: 22 base pairs (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic Primer"

(ix) FEATURE:
        (A) NAME/KEY: modified_base
        (B) LOCATION: 6
        (D) OTHER INFORMATION: /mod_base= i (ix) FEATURE:
        (A) NAME/KEY: modified_base
        (B) LOCATION: 18
        (D) OTHER INFORMATION: /mod_base= i (ix) FEATURE:
        (A) NAME/KEY: modified_base
        (B) LOCATION: 21
        (D) OTHER INFORMATION: /mod_base= i (xi) SEQUENCE DESCRIPTION: SEQ ID NO:4:

GAYGCNGARC ARGARCCNAC NG                            22

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic Primer"

(ix) FEATURE:
        (A) NAME/KEY: modified_base
        (B) LOCATION: 9
        (D) OTHER INFORMATION: /mod_base= i (ix) FEATURE:
        (A) NAME/KEY: modified_base
        (B) LOCATION: 12
        (D) OTHER INFORMATION: /mod_base= i (ix) FEATURE:
        (A) NAME/KEY: modified_base
        (B) LOCATION: 15
        (D) OTHER INFORMATION: /mod_base= i (ix) FEATURE:
        (A) NAME/KEY: modified_base
        (B) LOCATION: 18
        (D) OTHER INFORMATION: /mod_base= i (xi) SEQUENCE DESCRIPTION: SEQ ID NO:5:

CARGARCCNA CNGGNACNAA YGC                           23

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic Primer"

(xi) SEQUENCE DESCRIPTION: SEQ ID NO:6:

GGAAGAAGGC ACATGGC                                  17

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic Primer"

(xi) SEQUENCE DESCRIPTION: SEQ ID NO:7:

TATGGGGATT GGTGGCG                                      17

(2) INFORMATION FOR SEQ ID NO:8:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic Primer"

(xi) SEQUENCE DESCRIPTION: SEQ ID NO:8:

ACTCCTGGAG CCCGTC                                       16

(2) INFORMATION FOR SEQ ID NO:9:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic Primer"

(xi) SEQUENCE DESCRIPTION: SEQ ID NO:9:

AGACATGGCC TGCCCG                                       16

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic Primer"

(xi) SEQUENCE DESCRIPTION: SEQ ID NO:10:

GACACCAGAC CAACTGG                                     17

(2) INFORMATION FOR SEQ ID NO:11:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic Primer"

(xi) SEQUENCE DESCRIPTION: SEQ ID NO:11:

GGTAGCGACC GGCGC                                        15

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic Primer"

(xi) SEQUENCE DESCRIPTION: SEQ ID NO:12:

ACCTTTTCTA TCCTCCAGCA A                                           21

(2) INFORMATION FOR SEQ ID NO:13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic Primer"

(xi) SEQUENCE DESCRIPTION: SEQ ID NO:13:

GGGGAATTCC TTTCTCGGAC GCCTTGC                                     27

(2) INFORMATION FOR SEQ ID NO:14:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic Primer"

(xi) SEQUENCE DESCRIPTION: SEQ ID NO:14:

GGGGGTACCT AAAAATTGCT TCTTCCG                                     27

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic Primer"

(xi) SEQUENCE DESCRIPTION: SEQ ID NO:15:

GCCGGGCCCT ACTTCTCCGT T                                           21

(2) INFORMATION FOR SEQ ID NO:16:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic Primer"

(xi) SEQUENCE DESCRIPTION: SEQ ID NO:16:

GCGGGTACCT AATCATTTGT CATCGTCGTC CTTGTAGTCA AATTGCTTCT TCCGATTTTT  60

```
CC                                                              62
```

(2) INFORMATION FOR SEQ ID NO:17:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Asp Tyr Lys Asp Asp Asp Asp Lys
1               5
```

(2) INFORMATION FOR SEQ ID NO:18:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

```
GGAAAATTCG GAAGAAGCAA TTTGACTACA AGGACGACGA TGACAAATGA TAAGGTACCC    60

GC                                                                  62
```

(2) INFORMATION FOR SEQ ID NO:19:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Arg Lys Ile Arg Lys Lys Gln Phe Asp Tyr Lys Asp Asp Asp Asp Lys
1               5                  10                  15
```

METHOD FOR TREATING OPHTHALMIC DISEASES

TECHNICAL FIELD

The present invention relates to a therapeutic agent for ophthalmic diseases, which is effective for therapy of various retinochoroidal diseases.

BACKGROUND ART

Visual function is the most important in the sensory functions and 80% of information from the outer world is inputted through visual system. Therefore, visual dysfunction such as low vision or ablepsia is one of the most serious physical handicaps. In view of the fact that aging of people is proceeding in an information-oriented society, to prevent visual dysfunction would be one of the most important tasks of today's medicine. The importance of improving the QOL (quality of life) of patients in the treatment of the patients who have difficulties in daily life has been advocated. In ophthalmic diseases, it is essential to improve QOLV (quality of life and vision) including improvement and maintaining of visual function, so that it is an urgent task to establish a therapeutic method for attaining this.

Although severe low vision and ablepsia may be caused by various causes, those which are most likely to be the direct cause are retinochoroidal diseases including so called retinal neovascular diseases such as diabetic retinopathy and neovascular maculopathy; detachment of retina; choroiditis; and pigmentary retinal degeneration and macular dystrophy which are hereditary diseases. Therapies of these diseases include chemotherapies, photocoagulation operations and operations of hyaloid body. However, their effectiveness is not satisfactory and it is strongly demanded to develop a chemotherapy which is surely effective. When compared with the photocoagulation operations and operations of hyaloid body, which would accompany with invasion and serious stress, chemotherapy has great advantages that the invasion is smaller and to perform therapy is easier. Thus, development of chemotherapies against increasing various ophthalmic diseases is strongly desired. However, so far, the number of highly effective drugs is small.

On the other hand, with the recent progress of the basic and clinical studies, pathological clarification of retinochoroidal diseases is progressing. That is, it has been getting clearer that paropsis is caused not only by pathological change of visual cells in retina which is a sense organ in the narrow sense, but also by pathological change of retinal pigment epithelium which plays a great role in the metabolism of visual cells, disorders of nerve fibers, circulatory disorder of retina, and by circulatory disorder of choroid.

Especially, the important role of retinal pigment epithelial (RPE) cells in sustaining visual cells has been more and more clarified. That is, the cells are aligned in one layer, that is, in the lowest layer in the retina, on the Bruch's membrane, and absorb the light reached to the retina so as to prevent reflection. Further, the RPE cells constitute the blood-retinal barrier which partitions the visual cells and the vascular layer of choroid together with the Bruch's membrane, and participate in production of various cytokines. Thus, RPE cells have important physical and physiological functions, such as sustainment and regeneration of visual cells.

Recent studies revealed that the cytokines to which RPE cells relate include an accelerator and an inhibitor for neovascularization, so that RPE cells control generation, development, inhibition and degeneration of choroidal neovascularity (as a review article, Yasuhiko TANAKA, Ophthalmology, 31, 1233–1238, 1989; or Masanobu UYAMA, Journal of Japan Ophthalmology Association, 95, 1145–1180, 1991).

It is expected that cultivating RPE cells and making physiological and pathological studies on the RPE cells will greatly contribute to the clarification of physiological functions and pathological state of the eye, and to development of therapeutic methods. However, studies on the factors modifying functions of the RPE cells are in the beginning. It has been clarified only that interleukin (IL)-1β, IL-6, IL-8, TNF (tumor necrosis factor), GM-CSF (granulocyte-macrophage colony stimulating factor), MCP (monocyte chemotactic protein) and bFGF (basic fibroblast growth factor) stimulate the growth of RPE cells and TGF β (transforming growth factors-β) inhibits growth of RPE cells (Makoto TAMAI, Journal of Japan Ophthalmology Association, 97, 1–2, 1993). Further, these biological modifying factors have various actions, so that a selective pharmacological action on the RPE cells by these factors is not expected.

As described above, in spite of the fact that the retinochoroidal diseases which may cause serious visual dysfunction and ablepsia are expected to increase, sufficient therapeutic methods therefor have not been established, and histological and functional studies of the RPE cells which are thought to greatly influence on these diseases are now only in the beginning. Further, studies on therapy and prevention of retinochoroidal diseases by proliferation and activation of RPE cells have initiated.

As mentioned above, a task is to develop a factor which proliferates and activates RPE cells, as a therapeutic agent against retinochoroidal diseases against which no effective therapeutic drugs exist. Among the retinochoroidal diseases related to alteration of RPE cells, which accompany with serious visual dysfunction, pigmentary retinal degeneration, for example, is a hereditary disease. Only nosotropic treatments such as administration of a vasodilator or vitamin A are applied to this disease and there is no fundamental therapeutic method therefor. It is thought that a factor which proliferates and activates RPE cells may be a useful drug against such a disease.

On the other hand, as for retinopathy, maculopathy or dystrophy, which accompanies neovascularization, although photocoagulation by using laser beam may be effective in some cases, there are no fundamental chemotherapeutic methods so far. Although photocoagulation by laser beam has a hemostatic effect, heat coagulation spans to the inner layer of retina, so that the function of the retina is lost in a large area. Therefore, this method cannot be applied to cases where the diseased part is in the macular central pit which controls the central vision. Further, therapy by photocoagulatization cannot be performed in cases where choroidal neovascularity exists in the vicinity of central pit. Still further, it is problematic that recurrence of neovascularization often occurs after photocoagulation. Effective chemotherapy is demanded also in order to compensate these drawbacks of photocoagulation. Since RPE cells are known to produce an inhibitor for neovascularization in the growth phase (according to the review by UYAMA, infra), a growth factor of RPE cells may be used as an inhibitor for neovascularization, which may be applied to an alternative or combined therapy with photocoagulation.

In cases where primary or secondary retinal detachment is to be treated, a drug which promotes adhesion of retina is demanded. In cases where heat coagulation (diathermy), coagulation by freezing or photocoagulation is performed, which closes lacuna in the retina by cicatrization, a drug which promotes cicatrization is also demanded. In these cases, a drug which grows RPE cells that play a major role in cicatrization is thought to be applied as a therapeutic agent for detachment of retina.

Thus, developing a novel agent for growing RPE cells, which may be easily applied to intractable diseases such as retinopathy, maculopathy, retinal dystrophy, dystrophy and retinal detachment, is strongly demanded.

DISCLOSURE OF THE INVENTION

Accordingly, an object of the present invention is to provide a therapeutic agent for ophthalmic diseases, which is effective against the above-mentioned various retinochoroidal diseases.

That is, the present invention provides a therapeutic agent for ophthalmic diseases comprising as an effective ingredient a retinal pigment epithelial cell growth factor. The present invention also provides a growth-promoting agent for retinal pigment epithelial cells comprising as an effective ingredient tissue-factor-pathway-inhibitor-2.

The therapeutic agent for ophthalmic diseases according to the present invention is effective for treatment of various retinochoroidal diseases such as pigmentary retinal degeneration, retinopathy, maculopathy or retinal detachment.

BRIEF DESCRIPTION OF THE DRAWINGS

FIG. 1 shows (SEQ ID NO: 1) the amino acid sequence of the N-terminal region of tissue-factor-pathway-inhibitor-2, the nucleotide sequence of the primer used in the Examples (SEQ ID NOS: 4 & 5), as well as the relationship of their locations.

FIG. 3 shows the nucleotide sequence (SEQ ID NO: 2) of the cDNA of RPE cell growth factor prepared in the Examples of the present invention, as well as the deduced amino acid (SEQ ID NO: 3) sequence encoded thereby.

FIG. 5 shows the nucleotide sequence (SEQ ID NO: 18) of the 3'-end region of the cDNA used in constructing the vector expressing the cDNA of the RPE cell growth factor gene and the deduced amino acid sequence (SEQ ID NO: 19) encoded thereby, which vector was constructed in the Examples of the present invention.

BEST MODE FOR CARRYING OUT THE INVENTION

Figure 2:
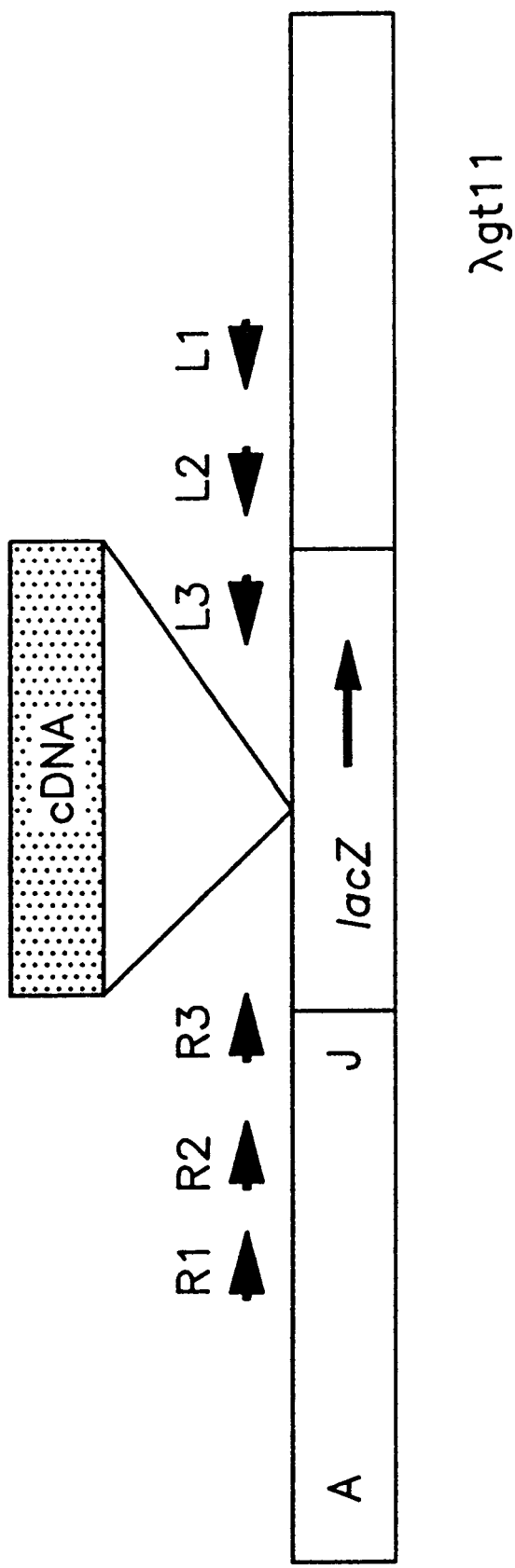
FIG. 2 shows the sites at which the primers used in the Examples of the present invention pairs in λgt11 phage DNA.

As mentioned above, the therapeutic agent for ophthalmic diseases according to the present invention comprises as an effective ingredient a retinal pigment epithelial cell growth factor. A preferred example of the retinal pigment epithelial cell growth factor which may be employed in the present invention is tissue-factor-pathway inhibitor-2, that is, placental protein 5. It is known that tissue-factor-pathway-2 (Sprecher et al., Proc. Natl. Acad. USA, 91, 3353–3357, 1994) has an activity to inhibit blood coagulation factor VIIa. Tissue-factor-pathway-2 was discovered as a serine protease inhibitor produced by T98G glioma cell, and its amino acid sequence was reported to be identical to that of placental protein 5 (Miyake et al., J. Biochem., 116, 939–942, 1994) related to blood coagulation. However, it has not been reported so far that these proteins have an activity to grow retinal pigment epithelial cells, and the fact that these proteins have an activity to grow retinal pigment epithelial cells was first discovered by the present inventors.

As mentioned above, tissue-factor-pathway inhibitor-2 and placental protein 5 (these are hereinafter also referred to as "RPE cell growth factor") per se, as well as production processes thereof are known. That is, RPE cell growth factor may be obtained by separation from culture supernatant of human cultured cells; by separation from cell extract or culture fluid of the cells prepared by the so called gene recombination technique using the cDNA of RPE cell growth factor; or by separation from the body fluid such as milk from a so called transgenic animal obtained by introducing an appropriate vector containing the cDNA of RPE cell growth factor into a fetal embryo. In the Examples described below, a method for obtaining RPE cell growth factor by separation from culture supernatant of human fibroblast cells, and a method for obtaining RPE cell growth factor by genetic engineering are concretely described.

In cases where the RPE cell growth factor is isolated from culture supernatant of human cultivated cells, which may be the cells derived from various normal tissues and may be established cell lines, which have abilities to produce RPE cell growth factor, and may preferably be epithelial cells, stromal cells and fibroblast cells. In cases where the RPE cell growth factor is prepared by utilizing genetic engineering technique, mammalian cells such as CHO (Chinese hamster ovary) cells, COS-1 (monkey kidney) cells, mouse C127 cells; cells of insects such as silk worm and Mamestra; or microorganisms such as E. coli, B. subtilis and yeasts may be employed as the host cells. Further, in cases where a transgenic animal is employed as a host, mouse, rat, hamster, rabbit, goat, sheep, swine, bovine or the like may be used as the host.

The thus prepared RPE cell growth factor may be purified and isolated from the cell culture supernatant, insect extract, bacterium extract or body extract by various chromatography. Any chromatography column may be used as long as it has an affinity to RPE cell growth factor. Examples of such a chromatography column may include columns having silica or calcium phosphate as an adsorbent; columns having heparin, a pigment or a hydrophobic group as a ligand; metal chelate columns; ion-exchange columns and gel permeation columns.

RPE cell growth factor may be widely applied to therapies of retinal pigmentary degeneration, retinal atrophia chorioideae and the like. More specifically, RPE cell growth factor may be applied to therapies of retinal pigmentary degeneration, Oguchi's disease, flecked retina, angioid streaks of retina, retinal pigment epitheliopathy (acute posterior multifocal placoid pigment epitheliopathy and multifocal posterior retinal pigment epitheliopathy), age-related macular degeneration, senile disciform macular degeneration, ocular histoplasmosis, central serous chorioretinopathy, central exudative chorioretinopathy, macular hole, mycopic macular atrophy, Stargardt disease, vitelliform macular degeneration and the like. Further, the RPE cell growth factor may be used as a therapy-promoting agent in therapies of idiopathic and secondary detachment of retina by photocoagulation.

The RPE cell growth factor may be administered orally or parenterally as it is or in the form of a pharmaceutical composition after being admixed with one or more pharmaceutically acceptable carriers or vehicles known in the art.

Examples of the formulations for oral administration include ointments, creams, injection solutions, poultices, liniments, suppositories, eye drops, formulations for pernasal absorption, formulations for transpulmonary absorption and formulations for percutaneous absorption. For ophthalmic use, examples of the formulations include injection solutions (for systemic administration, intravitreous administration, subretinal administration, injection into Tenon capsule, subconjunctival administration and the like), formulations for subkeratoconjunctival administration and eye drops. The solutions may be formulated by per se known methods. For example, RPE cell growth factor may be dissolved in an aseptic aqueous solution conventionally used for injection solutions, may be suspended in an extract, or may be encapsulated in liposomes after being emulsified. Solid formulations may be prepared by per se known methods. For example, a vehicle such as mannitol, trehalose, sorbitol, lactose or glucose may be added to the RPE cell growth factor and the resulting mixture may be lyophilized, thereby obtaining a solid formulation. The obtained solid formulation may be pulverized. Gel formulations may be prepared by per se known methods. For example, the RPE cell growth factor may be dissolved in a thickener or a polysaccharide such as glycerin, polyethylene glycol, methyl cellulose, carboxymethyl cellulose, hyaluronic acid or chondroitin sulfate, thereby obtaining a gel formulation.

To any of the formulations, human serum albumin, human immunoglobulin, α2 macroglobulin, an amino acid or the like may be added as a stabilizer. Further, an alcohol, sugar alcohol, ionic surface active agent, nonionic surface active agent or the like may be added as a dispersing agent or an absorbefacient in an amount not adversely affecting to the physiological activities of the RPE cell growth factor. Further, a trace mineral or an organic acid salt may be added as required.

RPE cell growth factor may be administered systemically or topically. Effective dose and number of times of administration differ depending on the type of formulation, administration route, age and body weight of patient, disease to be treated, symptom and severity of the disease. However, usually, 0.01 to 100 mg, preferably 0.1 to 10 mg of RPE cell growth factor may be administered once or in several times per an adult.

Since the fact that a RPE cell growth factor has an activity to grow retinal pigment epithelial cells was first discovered by the present inventors, the present invention also provides a method for growing retinal pigment epithelial cells comprising applying RPE cell growth factor to retinal pigment epithelial cells, and a growth-promoting agent for retinal pigment epithelial cells comprising as an effective component RPE cell growth factor. The growth-promoting agent comprises RPE cell growth factor in an appropriate carrier. As the carrier, the above-mentioned various vehicles may be employed, and appropriate buffer solutions such as physiological phosphate buffer is preferred. In this case, the concentration of RPE cell growth factor in the growth-promoting agent is not restricted, and usually about 10 ng/ml to 1 μg/ml, preferably about 50 ng/ml to 500 ng/ml. The effect to grow cells may usually be obtained by applying 1 ng to 100 ng, preferably 5 ng to 50 ng of the RPE cell growth factor per 10,000 retinal pigment epithelial cells.

EXAMPLES

The present invention will now be described by way of examples. It should be noted that the following examples are presented for the illustration purpose only and should not be interpreted in any restrictive way.

Example 1

Isolation and Purification of RPE Cell Growth Factor and Measurement of Activity Thereof 1. Isolation and Purification of RPE Cell Growth Factor Human fibroblast cells were inoculated to one liter of Eagle's MEM containing 5% fetal calf serum at the density of $1 \times 10^6$ cells/ml. The cells were cultivated in a 16 L glass culture vessel with contacting the cells on 0.3% micro carrier ("Cytodex 1", Pharmacia-Biotech) under stirring at 37° C. for 5 days. Then the culture medium was replaced with 14 liters of serum-free Eagle's MEM and 100 international units/ml of human interferon β was added. Twenty four hours later, poly(I):poly(C) was added to a concentration of 10 μg/ml, and another 2 hours later, the culture medium was replaced with Eagle's MEM containing a small amount of methyl cellulose, followed by continuing the culture for 6 days. After the culture, the micro carrier was precipitated and the supernatant was transferred to another vessel, which was used as a starting solution for purification. One hundred liters of the starting solution for purification was applied to S-Sepharose column (500 ml, Pharmacia-Biotech) and the column was washed with 5 liters of 10 mM phosphate buffer (PB)(pH7), followed by elution with 10 mM PB(pH7) containing 0.5 M NaCl. Two hundred milliliters of the peak fraction of protein was dissolved in 1M sodium sulfate solution (pH7) and the resulting solution was adsorbed to Polypropyl A column (0.8×25 cm, PolyLC), followed by elution with a concentration gradient (1–0M) of sodium sulfate.

Four milliliters of an active fraction detected by the method for measuring RPE cell growth factor activity, which method is hereinbelow described, was applied to a C4 reverse phase column (1×25 cm, Vydac) and elution was performed with a concentration gradient of water/acetonitrile containing 0.1% trifluoroacetic acid (pH 2). Two milliliters of an active fraction was concentrated to 100 μl under reduced pressure by Speed Vac concentrator.

Then the obtained concentrated active fraction was subjected to electrophoresis on polyacrylamide gel (PAGE) containing sodium dodecyl sulfate (SDS) under non-reduced condition according to Laemmli's method (Nature, 227, 680–685, 1970), thereby further purifying the protein. After the electrophoresis, the SDS-PAGE gel was sliced into 2 mm width and each sliced strip (1×2×4 mm) was immersed overnight in 0.5 ml of distilled water at 4° C. to elute the protein in the gel. The RPE cell growth activity of the eluted solution of the active fraction, which activity was measured by the method hereinbelow described in item 2, was 240 units/ml.

The fraction having RPE cell growth activity was moreover subjected to SDS-PAGE under non-reduced condition and then the gel was stained with silver. As a result, a single protein band was detected at the position corresponding to a molecular weight of 27,000±3,000. Five micrograms of the purified protein of this fraction was analyzed for its amino acid sequence by a protein sequencer (Applied Biosystems Model 470). As a result, it was confirmed that the amino acid sequence was identical to that of the tissue-factor-pathway inhibitor-2 described in Proc. Natl. Acad. USA, 91, 3353–3357, 1994 and identical to that of the placental protein 5 described in J. Biochem., 116, 939–942, 1994.

2. Measurement of RPE Cell Growth Activity

RPE cells of an established cell line K-1034 (Kigasawa et al., Jap. J. Ophthalmol. 38, 10–15, 1994) were placed in wells of a 24-well plastic plate at a population density of 1×104 cells/0.5 ml medium/well. As the culture medium, Dulbecco's MEM containing 5% fetal calf serum (FCS) was used. To each well, 2 μl of a test sample was added and the cells were cultivated at 37° C. for 5 days. After the culture, the number of cells was counted by a cell counter (Coulter Counter ZM Model), and the abundance ratio of the test group to the control group was calculated as the RPE cell growth factor ratio. The titer needed for doubling the number of cells was defined as 1 unit and the number of units was defined by multiplying the measured unit by the dilution.

Example 2
Cloning of cDNA of RPE Cell Growth Factor and Expression Thereof

Based on the amino acid sequence shown in SEQ ID NO. 1 in the Sequence Listing (i.e., the amino acid sequence of the N-terminal region of tissue-factor-pathway inhibitor-2), the following two types of primers 27S1 and 27S2 were designed and synthesized.

27S1 (SEQ ID NO: 4) GAT GCI GAA CAA GAA CCI ACI G CG GG

27S2 (SEQ ID NO: 5) CAA GAA CCI ACI GGI ACI AAT GC G G C

The primer 27S1 is a mixed primer corresponding to the amino acid sequence Asp Ala Glu Gln Glu Pro Thr Gly (residues 1–8 of SEQ ID NO: 1), and the primer 27S2 is a mixed primer corresponding to the amino acid sequence Gln Glu Pro Thr Gly Asn Ala (residues 4–8 and 10–11 of SEQ ID NO: 1). The relationships between the amino acid sequence shown in SEQ ID NO. 1 in the Sequence Listing and the primers 27S1 and 27S2 are shown in FIG. 1.

A cDNA library prepared by cloning human placental cDNA into λgt11 was purchased from Clonetech. Six types of primers R1, R2, R3, L1, L2 and L3 for amplifying the cloned cDNA by PCR method were synthesized. Nucleotide sequences of the primers are as follows:
R1 (SEQ ID NO: 6) GGA AGA AGG CAC ATG GC
R2 (SEQ ID NO: 7) TAT GGG GAT TGG TGG CG
R3 (SEQ ID NO: 8) ACT CCT GGA GCC CGT C
L1 (SEQ ID NO: 9) AGA CAT GGC CTG CCC G
L2 (SEQ ID NO: 10) GAC ACC AGA CCA ACT GG
L3 (SEQ ID NO: 11) GGT AGC GAC CGG CGC
The locations of the sites at which the primers hybridize in λgt11 are shown in FIG. 2.

The λgt11 into which human placental cDNA was cloned was infected to E. coli Y1090r[31], and DNAs were purified from proliferated phage. Using the purified DNAs as templates, and using primers R1 and L1 of λgt11, DNA was amplified by PCR. For the PCR, 0.2 μg of the template DNAs, 1.6 mM dNTPs, 1.0 μM of each of R1 and R2 primers, and 1 unit of Taq polymerase (TAKARA Ex Taq, TAKARA SHUZO) were used. The reaction was carried out initially at 94° C. for 5 minutes, and then a cycle of 94° C. for 30 seconds, 56° C. for 2 minutes and 72° C. for 8 minutes was repeated 25 times, followed by reaction at 72° C. for 7 minutes.

Then using a ¹⁄₁₀₀ aliquot of the amplified product as a template, the second PCR was performed using a combination of primers 27S1 and R2, or 27S1 and L2, under the same conditions as described above, thereby amplifying DNA. Further, using a ¹⁄₁₀₀ aliquot of the product of this second PCR, a third amplification of DNA was performed. That is, using a ¹⁄₁₀₀ aliquot of the reaction product produced by using the combination of primers 27S1 and R2, PCR was performed using primers 27S2 and R3 under the same conditions as described above, thereby amplifying DNA; and using a ¹⁄₁₀₀ aliquot of the reaction product produced by using the combination of primers 27S1 and L2, PCR was performed using primers 27S2 and L3 under the same conditions as described above, thereby amplifying DNA.

The DNA amplified by the third PCR was cloned into the Sma I site of pUC19 (Pharmacia) using Sure Clone ligation kit (Pharmacia). The cloned DNA was randomly sequenced to find a clone in the clones obtained by using the combination of primers 27S2 and R3, which clone codes for the amino acid sequence shown in SEQ ID NO. 1 in the Sequence Listing. This clone is called RPE1–3. The cDNA cloned in RPE-1 was sequenced.

To determine the nucleotide sequence of the region upstream of the nucleotide sequence corresponding to the amino acid sequence shown in SEQ ID NO. 1, a primer (called 1–3AS) corresponding to the hereinbelow described sequence in the cDNA was designed and synthesized. Its sequence is as follows:
ACC TTT TCT ATC CTC CAG CAA (SEQ ID NO: 12)
Using primers 1–3AS and L1, DNA was amplified by PCR. Reaction mixture was prepared by mixing 0.2 μg of template DNA (λgt11 DNA into which human placental cDNA was cloned), 1.6 mM dNTP, 1.0 μM each of primers 1–3AS and L1 and the buffer attached to Taq polymerase according to the instructions of the commercial product, and then 1 unit of Taq polymerase (TAKARA Ex Taq, TAKARA SHUZO) was added. After allowing to react at 94° C. for 5 minutes, a cycle of 94° C. for 30 seconds, 55° C. for 30 seconds and 72° C. for 30 seconds was repeated 25 times, followed by reaction at 72° C. for 7 minutes. The amplified DNA was cloned into the Sma I site of pUC19 by using Sure Clone ligation kit (Pharmacia). The DNA of a clone RPE1–3N which was one of the obtained clones was sequenced. As a result, the DNA of clone RPE1–3N contained a DNA sequence corresponding to the amino acid sequence shown in SEQ ID NO. 1, so that it was proved that RPE1–3N has a nucleotide sequence corresponding to the 5'-end of RPE cell growth factor.

From the sequences of RPE1–3 and RPE1–3N, the cDNA of RPE cell growth factor has a sequence shown in FIG. 3 or SEQ ID NO. 2 in the Sequence Listing.

The nucleotide sequence of the cDNA of the RPE cell growth factor was searched in a database. As a result, it was discovered that the RPE cell growth factor is tissue-factor-pathway inhibitor-2 (TFPI-2).

Figure 4:
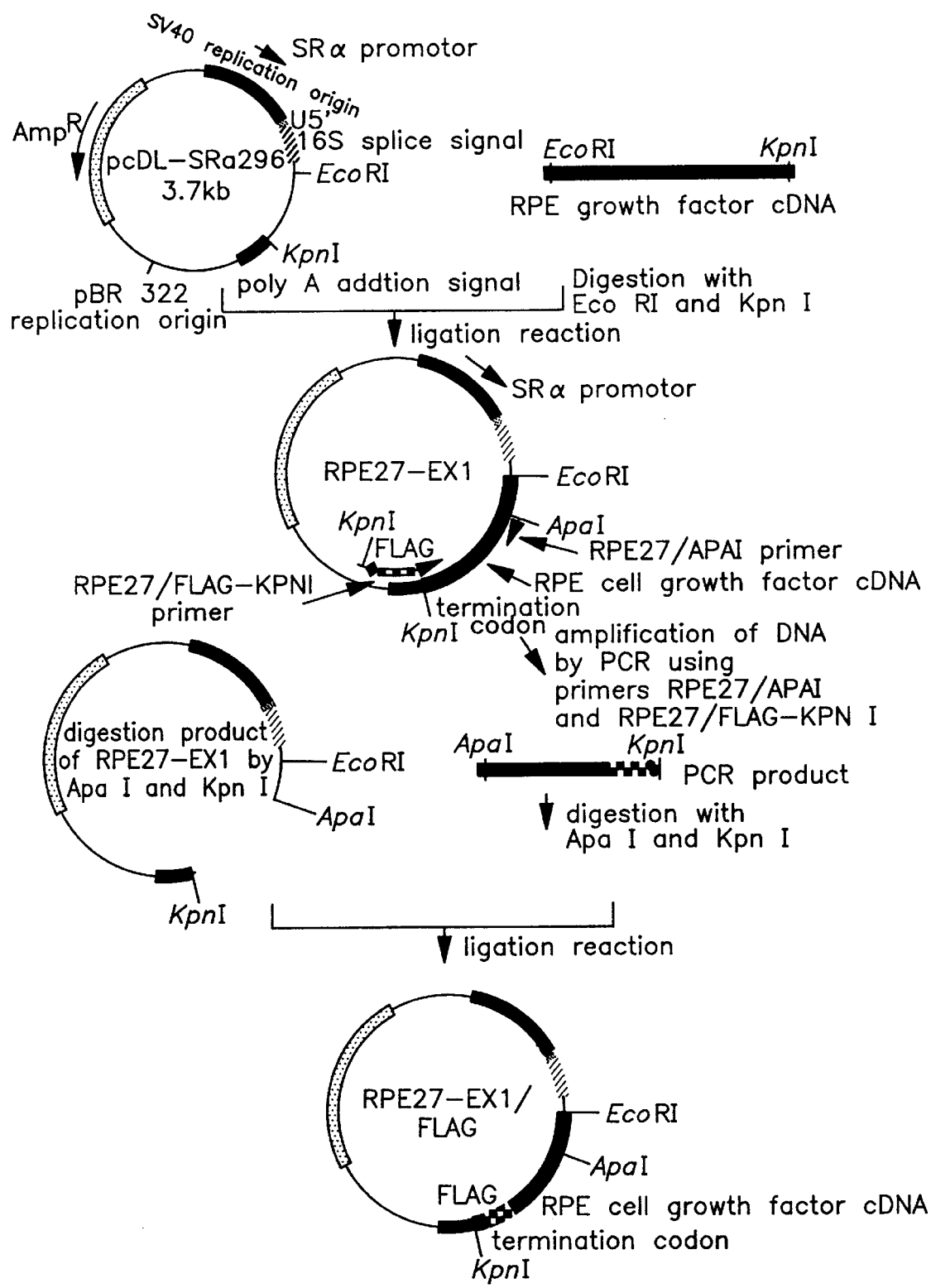
FIG. 4 shows the process for constructing a vector expressing the cDNA of the RPE cell growth factor gene, which vector was prepared in the Examples of the present invention.

2. Construction of Vector for Expressing RPE Cell Growth Factor/TFPI-2 in Animal Cells (see FIG. 4)

Primers having sequences corresponding to the 5'-end and 3'-end of this factor, respectively, were synthesized. The primer corresponding to the 5'-end is called RPE27-EX1 and that corresponding to the 3'-end is called RPE27-EX2. The sequences are as follows:
RPE27-EX1 (SEQ ID NO: 13) GGG GAA TTC CTT TCT CGG ACG CCT TGC

RPE27-EX2 (SEQ ID NO: 14) GGG GGT ACC TAA AAA TTG CTT CTT CCG

Reaction mixture was prepared by mixing 0.2 μg of template DNA (λgt11 DNA into which human placental cDNA was cloned), 1.6 mM dNTP, 1.0 μM each of primers RPE27-EX1 and RPE27-EX2 and the buffer attached to Taq polymerase according to the instructions of the commercial product, and then 1 unit of Taq polymerase (TAKARA Ex Taq, TAKARA SHUZO) was added. After allowing to react at 94° C. for 5 minutes, a cycle of 94° C. for 30 seconds, 55° C. for 1 minute and 72° C. for 2 minutes was repeated 25 times, followed by reaction at 72° C. for 7 minutes. The reaction product was digested with Eco RI and Kpn I to obtain a DNA fragment with a size of about 750 bp. A DNA fragment having a size of about 3.4 kbp obtained by digesting pcDL-SRα296 (FIG. 4, TAKEBE Y. et al., Mol. Cell Biol. 8, 466–472 (1988)) with Eco RI and Kpn I and the above-mentioned DNA fragment having a size of about 750 bp were ligated by T4 ligase. The obtained vector is called RPE27-EX1.

Means for facilitating purification after expression of RPE cell growth factor/TFPI-2 in animal cells was devised. That is, a chimeric protein having 8 amino acid residues attached to the C-terminal of the RPE cell growth factor/TFPI-2 is prepared. By so doing, the RPE cell growth factor/TFPI-2 may easily be purified by using an antibody against this 8 amino acid residues. It is known that addition of amino acid residues of about this size does not substantially influence on the activity.

To attach 8 amino acid residues to the C-terminal of the RPE cell growth factor/TFPI-2, DNA was amplified by PCR using RPE27-EX1 as a template. The used primers were RPE27/APAI (SEQ ID NO: 15) GCC GGG CCC TAC TTC TCC GTT and
RPE27/FLAG-KPNI (SEQ ID NO: 16) GCG GGT ACC TAA TCA TTT GTC ATC GTC GTC CTT GTA GTC AAA TTG CTT CTT CCG ATT TTT CC.
By using these primers, Asp Tyr Lys Asp Asp Asp Asp Lys (SEQ ID NO: 17) can be attached to the C-terminal of RPE cell growth factor/TFPI-2. Reaction mixture was prepared by mixing 0.2 μg of template DNA (RPE27-EX DNA), 1.6 mM dNTP, 1.0 μM each of primers RPE27/APAI and RPE27/FLAG-KPNI and the buffer attached to Taq polymerase according to the instructions of the commercial product, and then 1 unit of Taq polymerase (TAKARA Ex Taq, TAKARA SHUZO) was added. After allowing to react at 94° C. for 5 minutes, a cycle of 94° C. for 30 seconds, 56° C. for 1 minute and 72° C. for 2 minutes was repeated 25 times, followed by reaction at 72° C. for 7 minutes. The reaction product was digested with Apa I and Kpn I, and a DNA fragment having a size of about 570 bp was separated by agarose electrophoresis. The nucleotide sequence of the 3'-end region of this fragment and the amino acid sequence encoded thereby are shown in FIG. 5.

Then RPE27-EX1 was digested with Kpn I and Apa I and a DNA fragment having a size of about 3.5 kbp was separated by agarose gel electrophoresis. This DNA fragment and the above-mentioned fragment having a size of about 570 bp were ligated by T4 ligase. The obtained vector is called RPE27-EX/FLAG.

3. Expression of Human RPE Cell Growth Factor/TFPI-2 cDNA in Monkey COS-1 Cells

To 13 ml of RPMI1640 medium (Gibco) containing 50 mM Tris-HCl buffer (pH 7.4), 400 μg/ml of DEAE dextran (Pharmacia) and 100 μM of chloroquine (Sigma), 30 μg of the obtained RPE27-EX/FLAG was added, thereby obtaining a DNA mix. After washing the COS-1 cells (ATCC CRL-1650) grown to 70%–80% confluency in RPMI1640 medium containing 10% fetal calf serum (Gibco) in a 75 cm$^2$ culture flask (Corning) once with PBS, 8 ml of the above-described DNA mix was added, followed by culturing the cells in a 5% $CO_2$ incubator at 37° C. Four hours later, the DNA mix was removed and the cells were washed once with PBS. Then 30 ml of GIT medium (Nippon Seiyaku) was added to the cells and the cells were cultured in a 5% $CO_2$ incubator at 37° C. Four days later, the culture medium was recovered and 30 ml of fresh GIT medium was added, and culture was continued for additional 4 days. After the culture, the culture medium was recovered and combined with the culture medium recovered before.

4. Purification of Human RPE Cell Growth Factor/TFPI-2

From culture supernatant of the monkey COS-1 cells producing human RPE cell growth factor/TFPI-2 obtained in Section 3, recombinant human RPE cell growth factor/TFPI-2 was purified. That is, 120 ml of the culture supernatant of monkey COS-1 cells producing human RPE cell growth factor/TFPI-2 was filtered through a filter having a pore size of 0.2 μm and the filtrate was applied to 0.2 ml of anti-FLAG M2 affinity gel (EASTMAN KODAK) to which a monoclonal antibody against Asp Tyr Lys Asp Asp Asp Asp Lys (SEQ ID NO: 17) was attached. After washing with PBS the substances which were not adsorbed, the adsorbed substance was eluted by applying 0.1 M glycine-HCl buffer (pH 3.0). The eluted solution was sequentially recovered in 5 fractions of 1 ml each. From each fraction, an aliquot of 16 μl was taken and subjected to SDS-polyacrylamide gel electrophoresis under reduced condition. The recombinant human RPE cell growth factor/TFPI-2 to which the 8 amino acid residues were inserted exhibited a single band corresponding to a molecular weight of about 3200, and was recovered in the second fraction.

Example 3

1. Measurement of RPE Growth Activity

Figure 6:
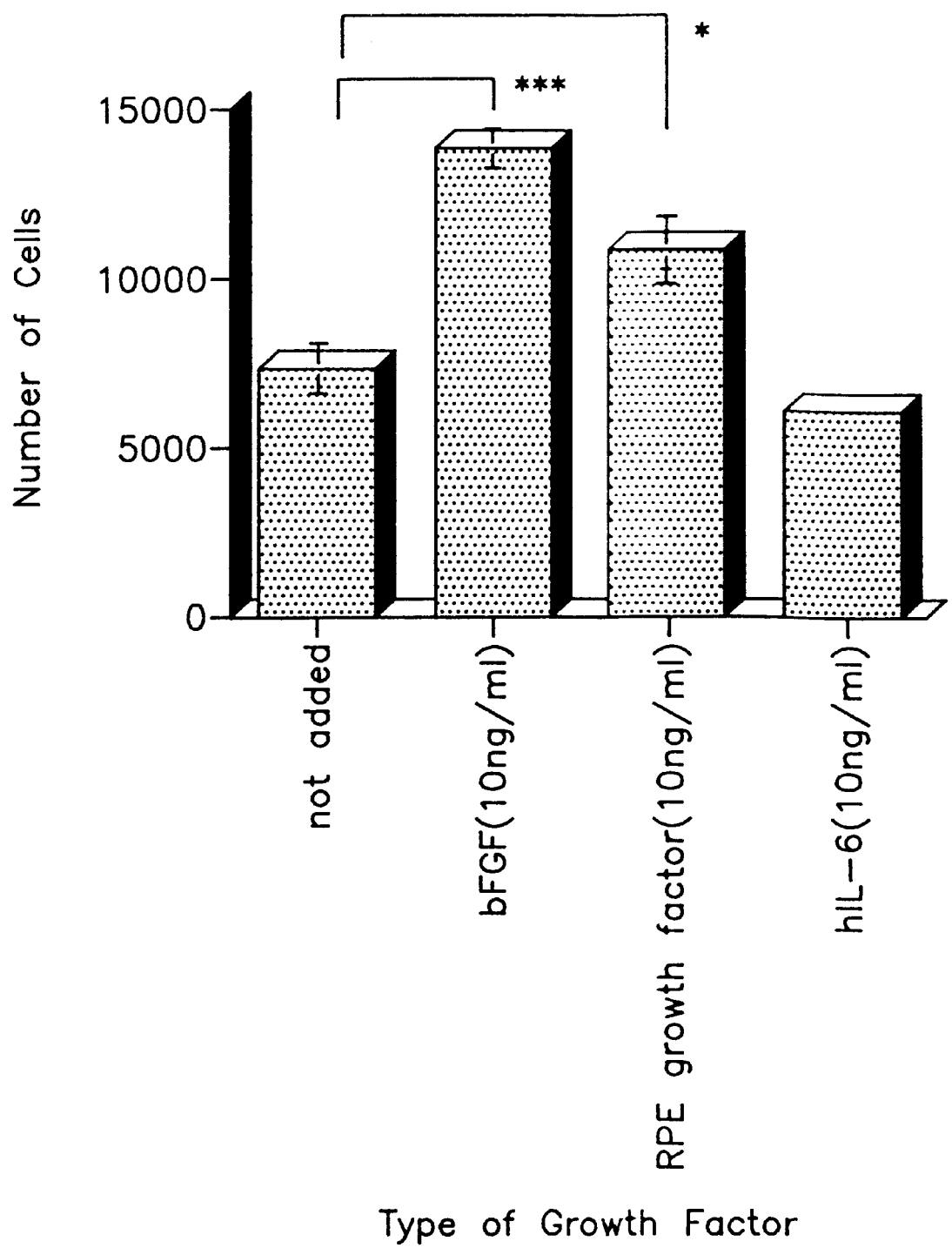
FIG. 6 shows the effect of the RPE cell growth factor for growing RPE cells, which was prepared in the Examples of the present invention, in comparison with the effect for growing RPE cells of other cell growth factors.

RPE cells were inoculated to CELGROSSER (SUMITOMO CHEMICAL) medium supplemented with 5% fetal calf serum placed in wells of a 24-well plate (CORNING) at a population density of 4500 cells/0.45 ml/well, and the cells were cultured at 37° C. in a 5% $CO_2$ incubator. On the next day, 0.05 ml of a sample was added and culture was continued for another 5 days. After the culture, the cells were dispersed by trypsin and the number of cells was counted by a cell counter (COULTER COUNTER ZM). The samples were 100 ng/ml of human basic fibroblast cell growth factor (bFGF, INTERGEN), 100 ng/ml of human interleukin 6 and 100 ng/ml of the recombinant human RPE cell growth factor/TFPI-2 purified in Example 2. As a control, CELGROSSER medium was used. As shown in FIG. 6, RPE cell growth factor/TFPI-2 significantly grew the cells.

2. Measurement of Fibroblast Cell Growth Factor

Figure 7:
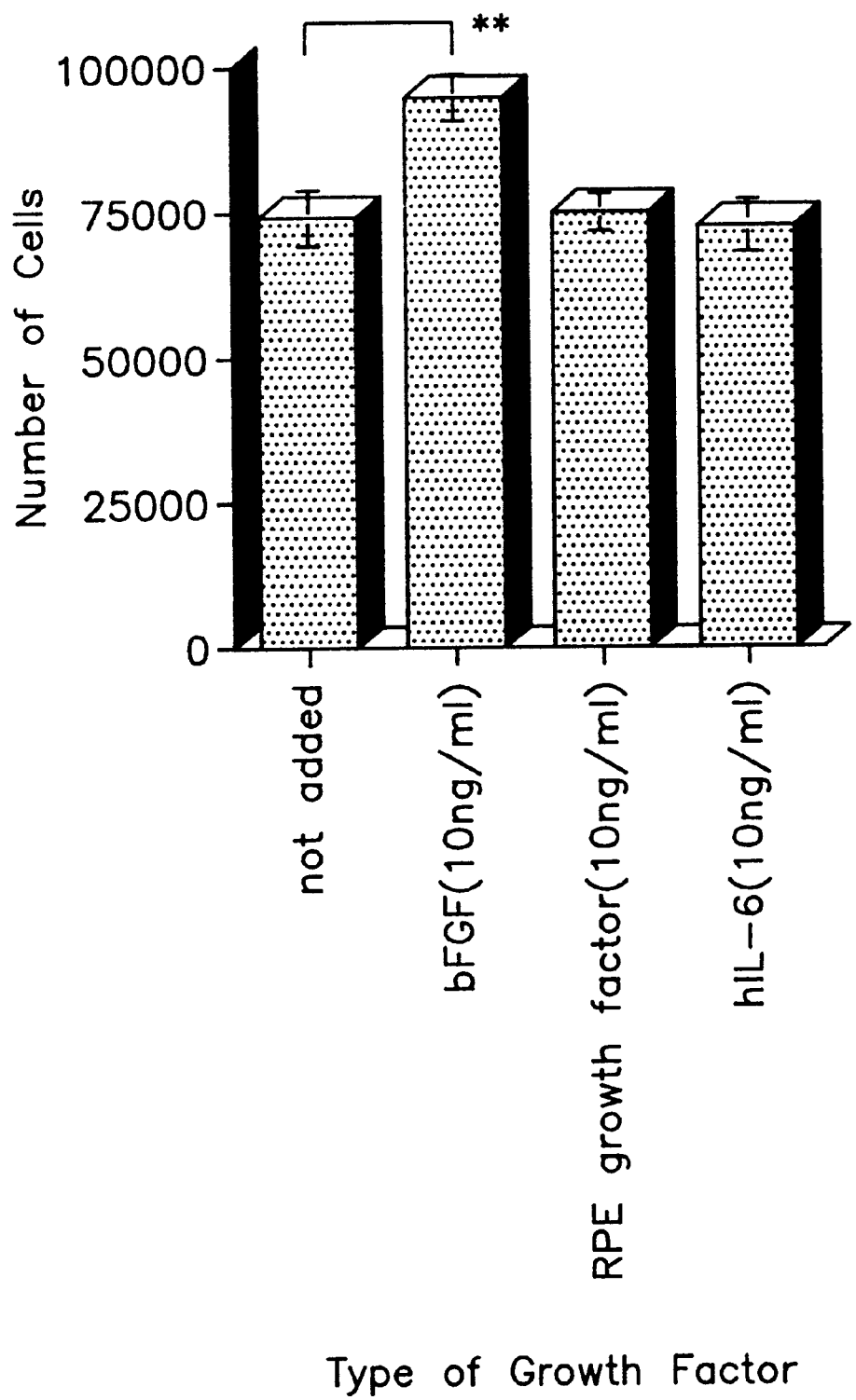
FIG. 7 shows the effect of the RPE cell growth factor for growing fibroblast cells, which was prepared in the Examples of the present invention, in comparison with the effect for growing fibroblast cells of other cell growth factors.

Fibroblast cells MRC5 (RCB0211) were inoculated to αMEM (GIBCO) containing 5% fetal calf serum, placed in wells of a 24-well plate (CORNING) at a population density of 4500 cells/0.45 ml/well, and the cells were cultured at 37° C. in a 5% $CO_2$ incubator. On the next days 0.05 ml of a sample was added and culture was continued for another 5 days. After the culture, the cells were peeled off by trypsin and the number of cells was counted by a cell counter (COULTER COUNTER ZM). The samples were 100 ng/ml of human basic fibroblast cell growth factor (bFGF, INTERGEN), 100 ng/ml of human interleukin 6 and 100 ng/ml of the recombinant human RPE cell growth factor/TFPI-2 purified in Example 2. As a control, αMEM was used. As shown in FIG. 7, bFGF significantly grew fibroblast cells, while RPE cell growth factor/TFPI-2 did not.

3. Measurement of Vascular Endothelium Growth Factor

Figure 8:
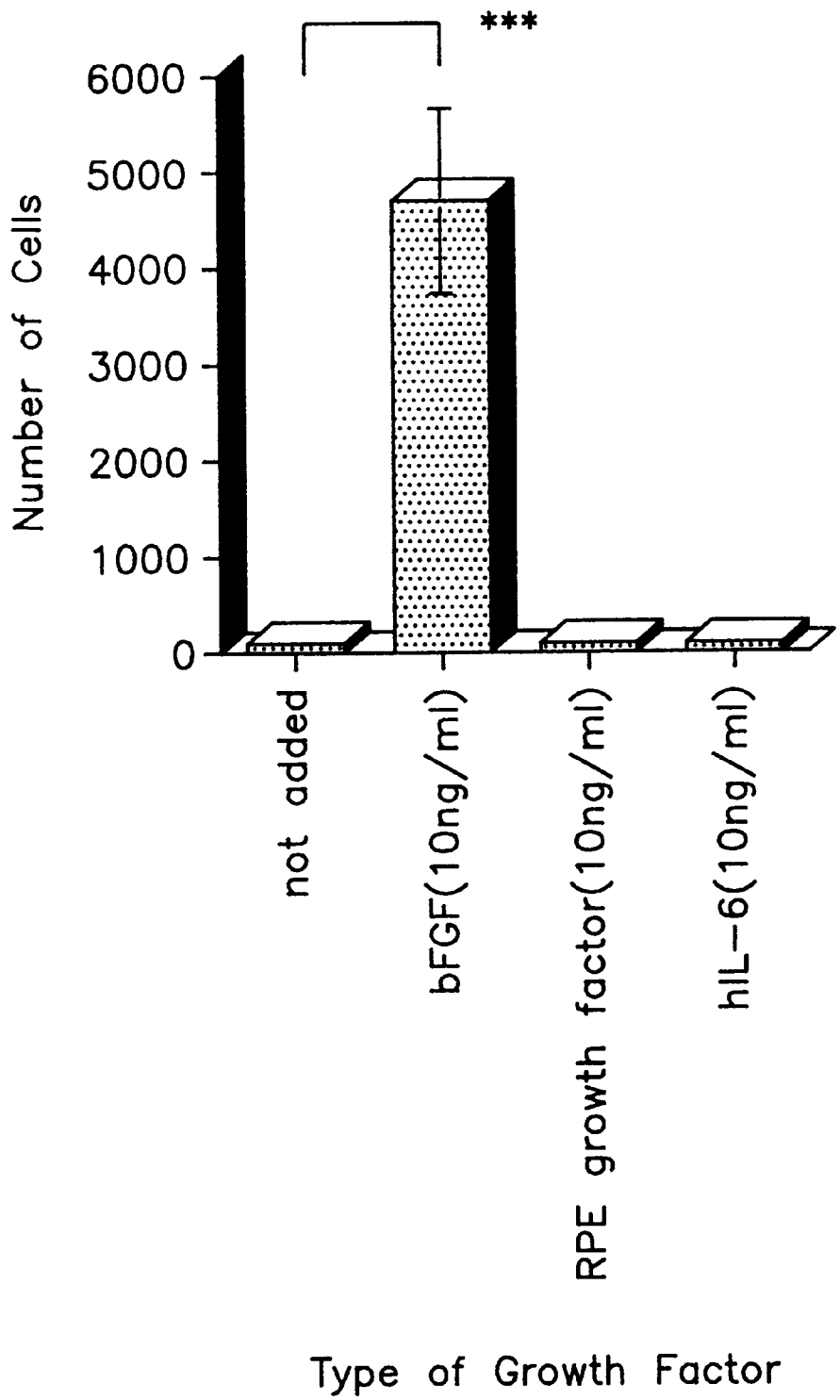
FIG. 8 shows the effect of the RPE cell growth factor for growing vascular endothelial cells, which was prepared in the Examples of the present invention, in comparison with the effect for growing the vascular endothelial cells of other cell growth factors.

Human umbilical cord vascular endothelial cells (CLONETICS) were inoculated to 199 medium (NISSUI) containing 5% fetal calf serum, placed in wells of a 24-well plate (CORNING) at a population density of 5000 cells/0.5 ml/well, and the cells were cultured at 37° C. in a 5% $CO_2$ incubator. Two hours later, the culture medium was removed and 0.5 ml of a sample was added, followed by continuing the culture for another 5 days. After the culture, the cells were peeled off by trypsin and the number of cells was counted by a cell counter (COULTER COUNTER ZM). The samples were 10 ng/ml of human basic fibroblast cell growth factor (bFGF, INTERGEN), 10 ng/ml of human interleukin 6 and 199 medium (containing 5% fetal calf serum) containing 10 ng/ml of the recombinant human RPE cell growth factor/TFPI-2 purified in Example 2. As a control, 199 medium (containing 5% fetal calf serum) was used. As shown in FIG. 8, bFGF significantly grew vascular endothelial cells, while RPE cell growth factor/TFPI-2 did not.

From the results described above, unlike bFGF, human RPE cell growth factor/TFPI-2 specifically grows RPE cells. Thus, since human RPE cell growth factor/TFPI-2 has a selective pharmacological effect on RPE cells, it was strongly suggested that human RPE cell growth factor/TFPI-2 may be used as a therapeutic agent for retinochoroidal diseases.

---

We claim:

1. A method for treating ophthalmic diseases comprising administering a protein comprising the amino acid sequence set forth in SEQ ID NO: 3 in an amount effective for growing retinal pigment epithelial cells to a patient suffering from an ophthalmic disease.

2. The method of claim 1 wherein said protein is administered orally or parenterally.

3. The method of claim 1 wherein said protein is administered systemically.

4. The method of claim 1 wherein said protein is administered topically.

5. A method for promoting the growth of retinal pigment epithelial cells comprising;

contacting retinal pigment epithelial cells with a protein comprising the amino acid sequence set forth in SEQ ID NO: 3 in an amount effective for growing retinal pigment epithelial cells.

6. The method of claim 1 wherein said ophthalmic disease is pigmentary retinal degeneration, retinopathy, maculopathy or retinal detachment.

\* \* \* \* \*